United States Patent [19]

Cutler

[11] Patent Number: 5,496,541

[45] Date of Patent: Mar. 5, 1996

[54] TASTEFUL TOOTHPASTE AND OTHER DENTAL PRODUCTS

[75] Inventor: Edward T. Cutler, Merion, Pa.

[73] Assignee: Pilot Research & Development Co., Merion, Pa.

[21] Appl. No.: 379,260

[22] Filed: Jan. 27, 1995

Related U.S. Application Data

[63] Continuation-in-part of Ser. No. 260,349, Jun. 15, 1994, abandoned, which is a continuation-in-part of Ser. No. 5,341, Jan. 19, 1993, abandoned.

[51] Int. Cl.$^6$ .............................. A61K 7/16; A61K 7/22
[52] U.S. Cl. ...................... 424/50; 424/43; 424/44; 424/48; 424/49; 424/53; 424/401; 424/466; 424/489; 424/499; 433/216; 426/3
[58] Field of Search ............................ 424/43, 44, 48, 424/49, 50, 53, 401, 466, 489, 499; 433/216; 426/3

[56] References Cited

U.S. PATENT DOCUMENTS

| | | | |
|---|---|---|---|
| 2,773,801 | 12/1956 | Fox | 424/48 |
| 3,691,272 | 9/1972 | Asche | 424/57 |
| 3,963,832 | 6/1976 | Hashimoto et al. | 424/49 |
| 4,022,881 | 5/1977 | Hawking | 424/49 |
| 4,110,429 | 8/1978 | Gaffar et al. | 424/54 |
| 4,206,198 | 6/1980 | Schmolka | 424/49 |
| 4,323,552 | 4/1982 | Schmolka | 424/49 |
| 4,343,785 | 8/1982 | Schmolka | 424/49 |
| 4,383,987 | 5/1983 | Kiozpeoplou | 424/49 |
| 4,407,788 | 10/1983 | Kiopeoplou | 424/49 |
| 4,465,661 | 8/1984 | Schmolka | 424/49 |
| 4,528,180 | 7/1985 | Schaeffer | 424/52 |
| 4,684,517 | 8/1987 | Clipper et al. | 424/52 |
| 4,980,152 | 12/1990 | Frazier et al. | 424/52 |
| 5,009,881 | 4/1991 | Hill et al. | 424/49 |
| 5,073,368 | 12/1991 | Subramanian | 424/58 |
| 5,085,853 | 2/1992 | Williams et al. | 424/53 |
| 5,096,698 | 3/1992 | Mitchell et al. | 424/49 |
| 5,096,699 | 3/1992 | Gaffar et al. | 424/49 |
| 5,176,901 | 1/1993 | Gallopo et al. | 424/49 |
| 5,192,529 | 3/1993 | Garlick et al. | 424/49 |

FOREIGN PATENT DOCUMENTS

| | | |
|---|---|---|
| 1176176 | 10/1984 | Canada . |
| 364245 | 4/1990 | European Pat. Off. . |
| 394470 | 10/1990 | European Pat. Off. . |
| 395287 | 10/1990 | European Pat. Off. . |
| 420408 | 4/1991 | European Pat. Off. . |
| 422803 | 4/1991 | European Pat. Off. . |
| 4494457 | 10/1991 | European Pat. Off. . |
| 0575137 | 12/1993 | European Pat. Off. . |
| 0577238 | 1/1994 | European Pat. Off. . |
| 59-104310 | 7/1982 | Japan . |
| 670297 | 11/1966 | South Africa . |
| 2142536 | 1/1985 | United Kingdom . |
| 2149661 | 6/1985 | United Kingdom . |
| 2210558 | 6/1989 | United Kingdom . |
| WO91/16033 | 10/1991 | WIPO . |
| 9311738 | 6/1993 | WIPO . |
| 9316680 | 9/1993 | WIPO . |
| 9316681 | 9/1993 | WIPO . |
| WO9412150 | 6/1994 | WIPO .............................. A61K 7/16 |

OTHER PUBLICATIONS

Baby Orajel Tooth & Gum Cleanser (Advertisement).

*Primary Examiner*—Ronald W. Griffin
*Attorney, Agent, or Firm*—Christopher Egolf

[57] ABSTRACT

Dental products employing a ternary surfactant system of poloxamers, anionic polysaccharides, and nonionic cellulose ethers. This ternary surfactant system has greatly enhanced foaming power relative to poloxamers alone or to poloxamers plus anionic polysaccharides or to poloxamers plus nonionic cellulose ethers. The poloxamer-anionic polysaccharide-nonionic cellulose ether surfactant system has little or no taste, is nonirritating, and has excellent adhesion to tooth surfaces and oral mucosa. Inclusion of a mild abrasive plus one or more of xylitol, raw licorice, licorice extract, and glycyrrhizin and its derivatives enhances the clinical efficacy of the formulations by further reducing plaque buildup thus brightening teeth and reducing tooth decay and periodontal disease.

The surfactant system can be used in a dentifrice paste or gel, powder, granules, disintegrable tablet, and a mouthwash, lozenge, and chewing gum.

11 Claims, 1 Drawing Sheet

TASTEFUL TOOTHPASTE AND OTHER DENTAL PRODUCTS

This application is a continuation-in-part of application Ser. No. 08/260,349, filed Jun. 15, 1994, which is a continuation-in-part of application Ser. No. 08/005,341, filed Jan. 19, 1993, now abandoned.

This invention relates to good tasting dental products having improved foaming properties. In particular this invention relates to dental products containing a poloxamer/anionic polysaccharide/non-ionic cellulose ether surfactant system, wherein the poloxamer, anionic polysaccharide and non-ionic cellulose ether are present in specific ratios.

BACKGROUND OF THE INVENTION

Surfactants play a key role in dentifrices. They emulsify fats and oils coating the oral cavity, they prevent dentifrice loss by drooling during brushing, and they provide a means for contacting active ingredients with teeth and gums during brushing. Unfortunately, most toothpaste surfactants have undesirable properties. They taste bad, both during and after brushing, and they irritate oral and gastric mucosa. Common dentifrice surfactants (for example, sodium lauryl sulfate, sodium N-lauroyl sarcosinate, etc) may even contribute to periodontal disease, which affects 75% of the U.S. population. These common surfactants cause chronic inflammation and sloughing of oral mucosa, thus facilitating infection by pathogenic microorganisms. See also: H. Bleeg, *Scand. J. Dent. Res.*, 98, 235 (1990). Current harsh surfactants may also aggravate tooth sensitivity and tooth staining in susceptible individuals.

PRIOR ART

Although hundreds of brands of toothpaste are sold in the United States today, nearly all of them use sodium lauryl sulfate as a surfactant because it is one of the cheapest, most efficient foaming agents known; however, it has the physiological incompatibilities previously mentioned. The fact that toothpaste does not taste good has been acknowledged in the patent literature (and, of course, consumers have known it all along).

Table 1 shows some of the surfactants previously proposed to replace sodium lauryl sulfate and sodium N-lauroyl sarcosinate. These replacements suffer from one or more of the following shortcomings: they are low foaming; they have not received FDA approval for oral use; and they do not taste good. The scientists at Lion Corporation (Tokyo, Japan) have dealt with the problem of bad tasting dentifrice surfactants by devising flavor/sweetener formulae to mask the unpleasant taste. Flavor masking has been traditionally accomplished by addition of strong flavors such as peppermint, menthol, wintergreen, spearmint, cinnamon, and clove. Lion has optimized this approach by using specific amounts of sweeteners such as xylitol, glycyrrhizin, stevioside, etc., or mixtures thereof, with specific amounts of flavors such as menthol, peppermint, anethole, cinnamaldehyde, etc., or mixtures thereof. For details see JP 54 26,339 (Feb. 27, 1979) and JP 60 130,509 (Jul. 12, 1985). Unfortunately, high concentrations of masking flavors may irritate the user, and cause the user to have unpleasant medicinal breath.

Poloxamers have been proposed as dentifrice surfactants. They are nearly tasteless and are FDA-approved for oral use. However, poloxamers are so low in foaming power as to render a dentifrice unsatisfactory from the standpoint of the user. In fact, poloxamers have rarely been used in commercial dentifrices as the major surfactant.

TABLE 1

| Patent | Surfactant | Taste |
|---|---|---|
| U.S. Pat. No. 4,130,636 December 19, 1978 | alkyl polyglycol-ether carboxylate | substantially tasteless, according to the inventor |
| U.S. Pat. No. 4,152,421 May 1, 1979 | mixtures of mono- and dialkylphosphate ester salts | tasteless or slightly bitter, according to the inventors |
| JP 79 117,039 September 11, 1979 | mixtures of sucrose fatty acid esters and Na N-acyl-L-glutamate | more pleasant than regular dentifrices, according to the inventors |
| U.S. Pat. No. 4,323,552 April 1, 1982 | block copolymers of butylene oxide and ethylene oxide | bland or tasteless, according to the inventor |
| U.S. Pat. No. 4,465,661 August 14, 1984 | ethoxylated fatty alcohols | free from the usual bitter surfactant taste, according to the inventor |
| JP 60 130,509 July 12, 1985 | sucrose fatty acid esters; | bitter, stinging; |
|  | fatty acid alkanolamides | bitter |
| U.S. Pat. No. 4,582,702 April 15, 1986 | poly(hydroxypropyl ether) | not unpleasant, according to the inventor |
| JP 61 152,622 July 11, 1986 | fatty acid alkanolamides | bitter |
| U.S. Pat. No. 5,017,364 May 21, 1991 | Na N-acyl-L-glutamate containing less than 1% free fatty acids | not unpleasant, according to inventor |
| U.S. Pat. No. 5,120,528 June 9, 1992 | $Na_2$ cocamide monoisopropanolamine sulfosuccinate; | acrid, bitter; |
|  | $Na_2$ oleamido PEG-2 sulfosuccinate; | bitter, soapy |
|  | $Na_2$ lauryl sulfosuccinate | bitter, stinging |
| DE 4,101,515 July 23, 1992 | alkyl ether sulfates | neutral taste and non-irritant, according to inventors |
| U.S. Pat. No. 5,190,747 March 2, 1993 | hexose fatty acid esters | little or no taste, according to the inventors |
| U.S. Pat. No. 5,292,502 March 8, 1994 | partially purified Na lauryl sulfoacetate + foam enhancers | substantially nonirritating, according to the inventors |

The patents in Table 2 disclose surfactant systems containing poloxamers plus nonionic cellulose ethers (NCE) plus a cosurfactant, wherein the cosurfactant plays the major role in foam production and poloxamer plays a minor role.

TABLE 2

Examples of Dental Product Surfactant Systems Wherein Poloxamer Plays a Minor Role

| Major Surfactant | Patent Which Mentions This Surfactant System |
|---|---|
| Anionic surfactant | U.S. Pat. No. 2,773,801 |
|  | U.S. Pat. No. 4,980,152 |
|  | U.S. Pat. No. 5,096,698 |
|  | EP 577,238 |
| Cationic surfactant | U.S. Pat. No. 4,110,429 |
|  | U.S. Pat. No. 5,176,901 |
| Amphoteric surfactant | U.S. Pat. No. 5,073,368 |
| Polysorbate | U.S. Pat. No. 4,684,517 |

The patents in Table 3 disclose surfactant systems containing poloxamers plus NCE plus agents which act as foam suppressors. These references acknowledge the poor foaming properties of poloxamer-containing surfactant systems. In fact, many of these patents teach the addition of a strongly foaming cosurfactant to boost the otherwise unacceptable foam to an acceptable level.

U.S. Pat. Nos. 4,980,152 and 5,085,853 disclose poloxamers and NCE together in one example, but in concentrations which lie outside the ranges claimed by my invention.

TABLE 3

Examples of Dental Product Surfactant Systems Containing Poloxamer plus a Nonionic Cellulose Ether plus a Foam Suppressor

| Foam Suppressor | US Patent Which Mentions This Surfactant System |
|---|---|
| sulfonated polyacrylate oligomer | U.S. Pat. No. 4,110,429 |
| polyacrylic acid | U.S. Pat. No. 4,980,152 |
| azacycloalkane-2,2-diphosphonic acid + synthetic anionic polymeric polycarboxylate | U.S. Pat. No. 5,096,699 |
| polydimethylsiloxane | U.S. Pat. No. 5,009,881 |

U.S. Pat. Nos. 3,963,832, 4,206,198, 4,323,552, 4,343,785, and 5,096,699, JP 59 104,310, EP 575,137, and WO 93 16,680 disclose poloxamers in a list of surfactants, and disclose NCE's and/or anionic polysaccharides (AP) in a list of binders, thickeners, or gelling agents, without recognizing the special or unexpected effects of the poloxamer-AP-NCE surfactant system and the enhanced foaming properties thereof.

EP 364,245 and 422,803, WO 91 16,033 and 93 16,681, and U.S. Pat. No. 5,176,901 specifically prohibit using AP's in dental formulations containing poloxamer plus NCE.

U.S. Pat. Nos. 4,022,881 and 5,192,529 disclose specific mixtures of NCE+AP used as a thickening system, but fail to mention poloxamer surfactants and thus fail to mention the poloxamer-AP-NCE surfactant system, with its unanticipated synergy.

Some patents have cited specific dental product formulations containing poloxamer and NCE. However, these specific formulations undergo syneresis within a few hours, due to the presence of incompatible ingredients. For example, in U.S. Pat. No. 4,110,429, the sulfonated polyacrylate oligomer causes syneresis. In U.S. Pat. No. 4,980,152, the presence of excessive amounts of poloxamer in the formulation causes syneresis (See Example 14F and Claims 4, 5 and 7 therein).

U.S. Pat. No. 3,691,272 (equivalent to ZA 670,297) discloses specific dentifrice formulations containing poloxamer+NCE, but not AP's. Thus, the poloxamer-AP-NCE surfactant system, with its unanticipated synergy, is not mentioned. Moreover, this reference teaches a poloxamer/NCE ratio outside that of my invention.

WO 93 11,738 discloses specific dentifrice formulations containing poloxamer+NCE or poloxamer+AP, but no formulation containing poloxamer+NCE+AP. Thus, the inventors indicate no awareness of the special or unexpected effects of the poloxamer-AP-NCE surfactant system, and never mention it. In addition, the poloxamer/NCE ratio of the examples is outside that of my invention.

According to the CTFA *Cosmetic Ingredient Handbook*, poloxamers are solubilizing and emulsifying agents; AP's and NCE's are emulsion stabilizers, film formers, and viscosity increasing agents. But AP's and NCE's are not listed as foam boosters.

Dow Chemical Company's *Formulator's Guide to METHOCEL Cellulose Ethers in Personal Care Products* mentions NCE's as thickeners for dentifrice and mouthwash, and as flavor oil emulsion stabilizers for mouthwash. And NCE's are cited as thickeners and foam enhancers for soaps and shampoos. But the poloxamer-AP-NCE surfactant system of my invention, with its unanticipated synergy, is not mentioned.

SUMMARY OF THE INVENTION

The subject of my invention is the poloxamer-anionic polysaccharide-nonionic cellulose ether surfactant system, whose components are:

poloxamer: A block copolymer of ethylene oxide (EO) and propylene oxide (PO), arranged as $(EO)_a(PO)_b(EO)_a$ wherein the PO content ranges from 15 to 85 mole percent, and the molecular weight ranges from 1,000 to 30,000.

anionic polysaccharide (AP): An anionic polysaccharide (in salt and/or acid form), naturally occurring or made by derivatizing a nonionic polysaccharide. Examples are alginic acid, gum arabic, carrageenan, carboxymethylcellulose, karaya gum, pectin, gum tragacanth, xanthan gum, or mixtures thereof.

Nonionic cellulose ether (NCE): The product formed by reacting alkali cellulose with alkyl halides and/or with alkylene oxides. Examples are methylcellulose, ethylcellulose, hydroxyethylcellulose, hydroxypropylcellulose, hydroxypropylmethylcellulose, or mixtures thereof.

The surfactant system of this invention consists of a ternary mixture of a poloxamer plus an anionic polysaccharide (AP) plus a nonionic cellulose ether (NCE) which, when added to a dental product in the proper amount, in the absence of any other surfactant, confers pleasing foaming properties. The surfactant system of this invention can be used to formulate such dental products as a dentifrice paste or gel, powder, granules, disintegrable tablet, and a mouthwash, lozenge and chewing gum.

The surfactant system of this invention has little or no taste (no masking flavor is necessary), is nonirritating, and its ingredients have already received FDA approval for oral use. Products that employ the poloxamer-AP-NCE surfactant system can be made sufficiently pleasant tasting for the user to enjoy food immediately after using them.

It is an object of the invention to provide a good tasting dental product that provides acceptable foaming properties.

DETAILED DESCRIPTION OF THE INVENTION AND THE PREFERRED EMBODIMENTS

Figure 1:
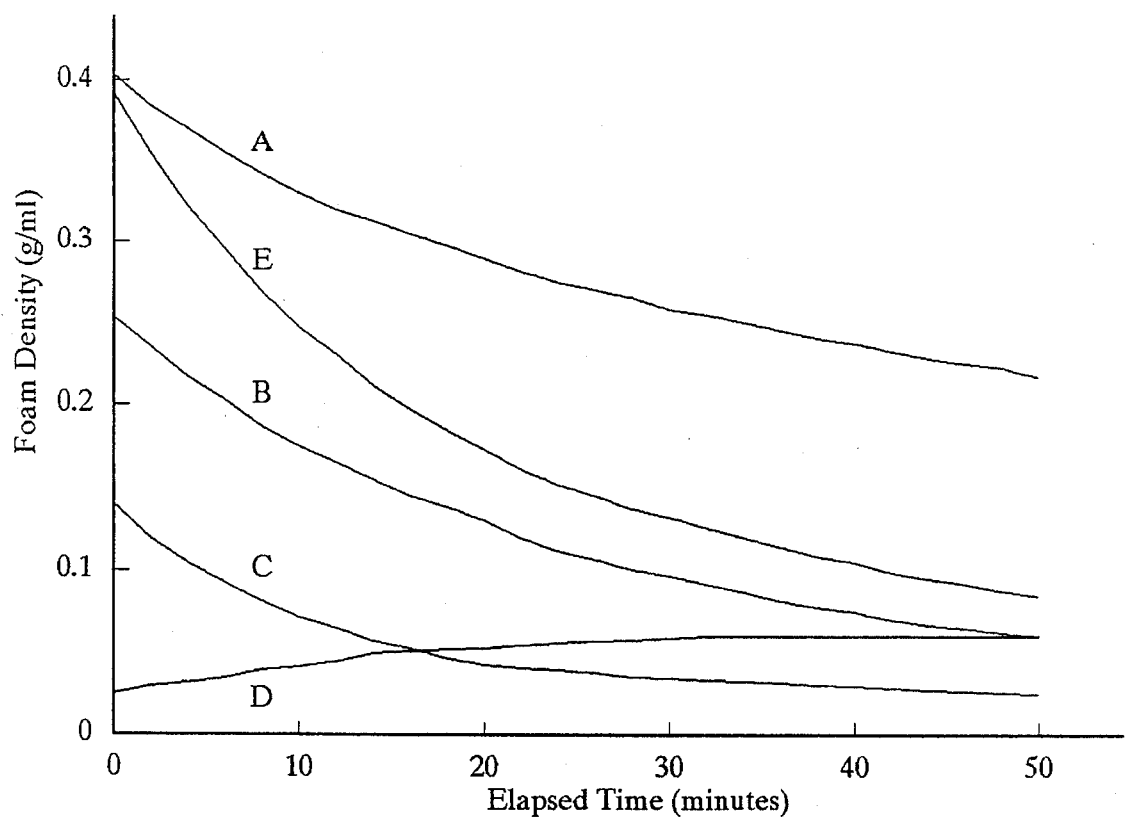
FIG. 1 is a graph comparing the foam density of the surfactant system according to the invention with the foam densities of the components of the surfactant system.

The surfactant system utilized in dental products according to the invention is made by mixing 0.01 to 10% by weight of poloxamer, or a mixture of poloxamers, plus an AP, or a mixture of AP's, plus a NCE, or a mixture of NCE's. The poloxamer/AP ratio should be greater than 1; the AP/NCE ratio should be greater than 1. Poloxamer/NCE ratios of less than 1 decrease the foamability of poloxamer.

Suitable poloxamers include but are not limited to any of the products sold under the tradename "Pluronic" by BASF Performance Chemicals (Parsippany, N.J.).

Suitable anionic polysaccharides include but are not limited to any of the natural or derivatized anionic polysaccharide polymers such as carboxymethylcellulose, carboxymethylmethylcellulose, carboxymethylhydroxyethylcellulose, alginic acid, gum arabic, carrageenan, karaya gum, pectin, gum tragacanth, and xanthan gum.

Suitable nonionic cellulose ethers include but are not limited to any of the products sold under the tradename "Methocel" by Dow Chemical Co. (Midland, Mich.) or under the tradenames "Benecel," "Klucel," and "Natrosol" by Aqualon Co. (Wilmington, Del.), such as methylcellulose, ethylcellulose, hydroxyethylcellulose, hydroxypropylcellulose, hydroxyethylmethylcellullose, hydroxyethylethylcellulose, and hydroxypropylmethylcellulose.

An example of the foaming behavior of the ternary surfactant system of this invention is shown in FIG. 1. For each experiment, a graduated cylinder of 50 ml capacity, containing 25 ml of aqueous poloxamer solution, was shaken for 60 seconds and then allowed to stand. The reagents were:

poloxamer=Pluronic F127 (BASF Performance Chemicals, Parsippany, N.J.)

anionic polysaccharide=sodium carboxymethylcellulose, grade 7MF (Aqualon Co., Wilmington, Del.)

nonionic cellulose ether=hydroxypropylmethylcellulose, grade Methocel K15MP (Dow Chemical Co., Midland, Mich.)

The solutions examined were:

| Curve | Solution Composition |
|---|---|
| A | 2% poloxamer + 0.5% AP + 0.4% NCE |
| B | 2% poloxamer + 0.4% NCE |
| C | 2% poloxamer + 0.5% AP |
| D | 2% poloxamer |
| E | arithmetic sum of curve B + curve C (this is an expected curve, not an actual result) |

A number of conclusions can be drawn from FIG. 1. The system with the lowest foam density is aqueous 2% poloxamer (curve D). The poloxamer-AP-NCE surfactant system (curve A) yields a foam with higher density for a much longer duration than either the poloxamer-NCE system (curve B) or the poloxamer-AP system (curve C). Assuming foam density is a linear function of the reagents added to aqueous poloxamer, the expected result of mixing poloxamer+AP+NCE (curve E) is the arithmetic sum (curve B+curve C). However, the actual result of mixing poloxamer+AP+NCE (curve A) shows a much greater foam density persistence over time than would be expected in a linearly dependent system. This result is a totally unanticipated synergy.

When toothpastes were made with the surfactant systems of FIG. 1 and tested clinically, without revealing their identities, the evaluators expressed a preference for the toothpaste containing the poloxamer-AP-NCE surfactant system.

Additional unanticipated aspects of the surfactant system of my invention include such clinical benefits as nonirritancy, prevention and reduction of plaque buildup, prevention and reduction of tooth staining, prevention and reduction of tooth sensitivity, and excellent adhesion to tooth surfaces and oral mucosa, which enhances the beneficial effects of the surfactant system and the other active ingredients in the formulation. Inclusion of significant quantities of one or more of xylitol, raw licorice, licorice extract, glycyrrhizin and its derivatives (pure or impure, in acid, salt, or ester form) enhances the clinical efficacy of the formulations of the present invention (without materially affecting foam production) by further reducing the buildup of plaque, thus brightening teeth and reducing tooth decay and periodontal disease.

In addition to the surfactant system of this invention, other dental product ingredients may include:

a. 5 to 60% by weight of one or more of the known polyol humectants selected from glycerol, xylitol, sorbitol, mannitol, and polyethylene glycol.

b. 0.001 to 5% by weight of one or more of the known natural and artificial sweeteners selected from xylitol, saccharin, aspartame, raw licorice, licorice extract, glycyrrhizin and its derivatives (pure or impure, in acid, salt, or ester form).

c. additional ingredients, depending on the embodiment, including:

(i) flavoring agents such as mint, spearmint, peppermint, orange wintergreen, and known flavoring agent, (ii) plaque preventatives, (iii) abrasives, for example, calcium carbonate, dibasic calcium phosphate, tribasic calcium phosphate, calcium pyrophosphate, hydroxyapatite, alumina, silica, titania and fluorapatite, (iv) water, (v) thickening agents, for example, silicas, (vi) gum bases, for example chicle or a polybutene, (vii) fluoride agents, for example sodium fluoride and sodium monofluorophosphate, (viii) tablet lubricants, for example, calcium stearate, magnesium stearate, hydrogenated vegetable oil, and beeswax, (ix) mono-, di- or polydentate acids, or salt thereof, for example, citric acid, ethylenediaminetetraaceticacid, ascorbic acid, and sulfuric acid, (x) preservatives, for example, one or more of the parabens, potassium sorbate and calcium propionate, (xi) antioxidants, for example, alpha-tocopherol, beta-carotene, and ascorbic acid.

Preferred embodiments of the invention contain no foam supressors, in particular, preferred embodiments exclude polyacrylates, sulfonated polyacrylate oligomers, polydimethylsiloxanes, azacycloalkane-2,2-diphosphonic acids, synthetic anionic polymeric polycarboxylates, and the like.

EXAMPLE 1

Dentifrice Powder, Granules, or Disintegrable Tablets

| Ingredient | Weight % |
|---|---|
| calcium carbonate | 50.0 |
| xylitol | 31.0 |
| microcrystalline cellulose | 14.6 |
| Pluronic F127 | 2.0 |
| xanthan gum | 1.0 |
| Methocel K15MP | 0.5 |
| flavor | 0.5 |
| monoammonium glycyrrhizinate | 0.4 |

If desired, the granules can be blended with 0.5% by weight of a tablet lubricant and compressed into a tablet which disintegrates in the mouth and can then be chewed into a paste.

EXAMPLE 2A

Dentifrice Paste

One of the embodiments of this invention is a dentifrice in paste form. A typical formula for a dentifrice paste according to the claims of this invention is:

| Ingredient | Weight % |
| --- | --- |
| xylitol | 35.9 |
| water | 33.4 |
| calcium carbonate | 24.1 |
| Pluronic F127 | 4.0 |
| cellulose gum (Aqualon 7MF) | 1.5 |
| Methocel K15MP | 0.5 |
| dipotassium glycyrrhizinate | 0.4 |
| flavor | 0.2 |

EXAMPLE 2B

Dentifrice Gel

One of the embodiments of this invention is a dentifrice in gel form. A typical formula for a dentifrice gel according to the claims of this invention is:

| Ingredient | Weight % |
| --- | --- |
| xylitol | 38.0 |
| water | 33.3 |
| thickening silica* | 10.0 |
| glycerin | 7.3 |
| abrasive silica** | 5.0 |
| Pluronic F127 | 4.0 |
| cellulose gum (Aqualon 7MF) | 1.5 |
| Methocel K15MP | 0.5 |
| disodium glycyrrhizinate | 0.2 |
| flavor | 0.2 |

*Zeofree 153 (J. M. Huber Co., Havre de Grace, MD)
**Sylodent 700 (W. R. Grace Co., Baltimore, MD)

EXAMPLE 3

Dentifrice Lozenge

One of the embodiments of this invention is a plaque preventing hard or soft lozenge to be sucked on by the user. A typical formula for a lozenge according to the claims of this invention is:

| Ingredient | Weight % |
| --- | --- |
| xylitol | 91.6 |
| Pluronic F127 | 4.0 |
| cellulose gum (Aqualon 7MF) | 1.0 |
| Methocel K15MP | 0.5 |
| calcium carbonate | 2.0 |
| flavor | 0.5 |
| dipotassium glycyrrhizinate | 0.4 |

EXAMPLE 4

Dentifrice Chewing Gum

One of the embodiments of this invention is a plaque preventing chewing gum. A typical formula for a chewing gum according to the claims of this invention is:

| Ingredient | Weight % |
| --- | --- |
| gum base | 20.0 |
| xylitol | 67.5 |
| calcium carbonate | 5.0 |
| glycerin | 3.0 |
| Pluronic F127 | 2.0 |
| cellulose gum (Aqualon 7MF) | 1.0 |
| Methocel K15MP | 0.5 |
| flavor | 0.5 |
| monoammonium glycyrrhizinate | 0.4 |
| xanthan gum | 0.1 |

EXAMPLE 5

Mouthwash

One of the embodiments of this invention is a plaque preventing mouthwash. A typical formula for a mouthwash according to the claims of this invention is:

| Ingredient | Weight % |
| --- | --- |
| water | 65.49 |
| xylitol | 32.1 |
| Pluronic F127 | 1.0 |
| cellulose gum (Aqualon 7MF) | 0.24 |
| Methocel K15MP | 0.12 |
| flavor | 0.5 |
| disodium glycyrrhizinate | 0.4 |
| preservative | 0.1 |
| sodium fluoride | 0.05 |

I claim:

1. Dental products comprising a surfactant system employing poloxamers as the main surfactant, wherein said poloxamer comprises 0.01 to 10 weight % of said dental product, said system further comprising anionic polysaccharides (AP) plus nonionic cellulose ethers (NCE) in a ternary surfactant system having enhanced foaming power relative to poloxamers alone or to poloxamers plus anionic polysaccharide or to poloxamers plus nonionic cellulose ethers, wherein the weight ratio of said poloxamer to said anionic polysaccharides is greater than 1, and the weight ratio of said anionic polysaccharide to said nonionic cellulose ether is greater than 1.

2. A dental product according to claim 1, wherein the poloxamer consists of a block copolymer of ethylene oxide and propylene oxide arranged as $(EO)_a(PO)_b(EO)_a$ wherein the PO content ranges from 15 to 85 mole percent, and the molecular weight ranges from 1,000 to 30,000.

3. A dental product according to claim 1, wherein said anionic polysaccharides are selected from the group consisting of alginic acid, gum arabic, carrageenan, carboxymethylcellulose, karaya gum, pectin, gum tragacanth, and xanthan gum.

4. A dental product according to claim 1, wherein the nonionic cellulose ether is selected from the group consisting of alkylated celluloses and hydroxyalkylated celluloses, wherein said hydroxyalkylated cellulose is selected from the group consisting of methylcellulose, ethylcellulose, hydroxyethylcellulose, hydroxypropylcellulose, and hydroxypropylmethylcellulose.

5. A dental product according to claim 1 wherein said dental product is selected from the group consisting of dentifrice powders, granules, disintegrable tablets, dentifrice pastes or gels, dentifrice lozenges, dentifrice chewing gums, and mouthwashes.

6. A dental product according to claim 1 which is essentially free of all surfactants other than those in the ternary surfactant system of poloxamers, anionic polysaccharides, and nonionic cellulose ethers.

7. A dental product according to claim 6 from which are excluded all foam suppressors selected from the group consisting of polyacrylates, sulfonated polyacrylate oligomers, polydimethylsiloxanes, azacycloalkane-2,2-diphosphonic acids, and synthetic anionic polymeric carboxylates.

8. A dental product according to claim 1, further comprising:
   a. 5 to 60% by weight of polyol humectants selected from the group consisting of glycerol, xylitol, sorbitol, mannitol, and polyethylene glycol,
   b. 0.001 to 5% by weight of sweeteners selected from the group consisting of xylitol, saccharin, aspartame, raw licorice, licorice extract, glycyrrhizin and its derivatives.

9. A dental product according to claim 8 further comprising one or more of the following ingredients:
   a. 1 to 60% by weight of a mild abrasive selected from the group consisting of calcium carbonate, dibasic calcium phosphate, tribasic calcium phosphate, calcium pyrophosphate, and hydroxyapatite, having a hardness less than or equal to that of tooth enamel,
   b. 1 to 60% by weight of a strong abrasive selected from the group consisting of alumina, silica, titania and fluorapatite having a hardness greater than that of tooth enamel,
   c. 0.1 to 10% by weight of flavor,
   d. 1 to 2000 ppm by weight of a fluoride containing compound selected from the group consisting of sodium fluoride and sodium monofluorophosphate,
   e. 0.1 to 10% by weight of a mono-, di, or polydentate acid or its salts selected from the group consisting of citric acid, ethylenediaminetetraacetic acid, ascorbic acid, and sulfuric acid to adjust and maintain the pH between 6 and 10,
   f. 0.1 to 1.0% by weight of preservative selected from the group consisting of paraben, potassium sorbate and calcium propionate, and
   g. 0.1 to 1.0% by weight of antioxidant selected from the group consisting of alphatocopherol, beta-carotene, and ascorbic acid,
   h. 5 to 95% by weight of water
   i. 0.1 to 10% of a thickener selected from the group consisting of colloidal cellulose, hydrated silica, polyethyleneglycol, and polyvinylpyrrolidone.

10. A dental product according to claim 8 in the form of a dentifrice chewing gum further comprising 5 to 60% of gumbase selected from the group consisting of chicle and polybutenes.

11. A dental product according to claim 9 in the form of a dentifrice tablet, further comprising 0.1 to 1.0% by weight of a tablet lubricant selected from the group consisting of calcium stearate, magnesium stearate, hydrogenated vegetable oil, and beeswax.

* * * * *

REEXAMINATION CERTIFICATE (4384th)
United States Patent
Cutler

(10) Number: US 5,496,541 C1
(45) Certificate Issued: Jun. 26, 2001

(54) TASTEFUL TOOTHPASTE AND OTHER DENTAL PRODUCTS

(75) Inventor: Edward T. Cutler, Merion, PA (US)

(73) Assignee: Squigle, Inc., Narberth, PA (US)

Reexamination Request:
No. 90/005,272, Feb. 25, 1999

Reexamination Certificate for:
Patent No.: 5,496,541
Issued: Mar. 5, 1996
Appl. No.: 08/379,260
Filed: Jan. 27, 1995

Related U.S. Application Data

(63) Continuation-in-part of application No. 08/260,349, filed on Jun. 15, 1994, now abandoned, which is a continuation-in-part of application No. 08/005,341, filed on Jan. 19, 1993, now abandoned.

(51) Int. Cl.$^7$ ............................. A61K 7/16; A61K 7/18
(52) U.S. Cl. ............................................. 424/49; 424/52
(58) Field of Search ................................... 424/49–58

(56) References Cited

U.S. PATENT DOCUMENTS

4,664,906  5/1987  Sipos ..................................... 424/49

OTHER PUBLICATIONS

CTFA International Cosmetic Ingredient Dictionary, Fourth Ed., 1991, pp. 449 and 992.

*Primary Examiner*—Shep Rose

(57) ABSTRACT

Dental products employing a ternary surfactant system of poloxamers, anionic polysaccharides, and nonionic cellulose ethers. This ternary surfactant system has greatly enhanced foaming power relative to poloxamers alone or to poloxamers plus anionic polysaccharides or to poloxamers plus nonionic cellulose ethers. The poloxamer-anionic polysaccharide-nonionic cellulose ether surfactant system has little or no taste, is nonirritating, and has excellent adhesion to tooth surfaces and oral mucosa. Inclusion of a mild abrasive plus one or more of xylitol, raw licorice, licorice extract, and glycyrrhizin and its derivatives enhances the clinical efficacy of the formulations by further reducing plaque buildup thus brightening teeth and reducing tooth decay and periodontal disease.

The surfactant system can be used in a dentifrice paste or gel, powder, granules, disintegrable tablet, and a mouthwash, lozenge, and chewing gum.

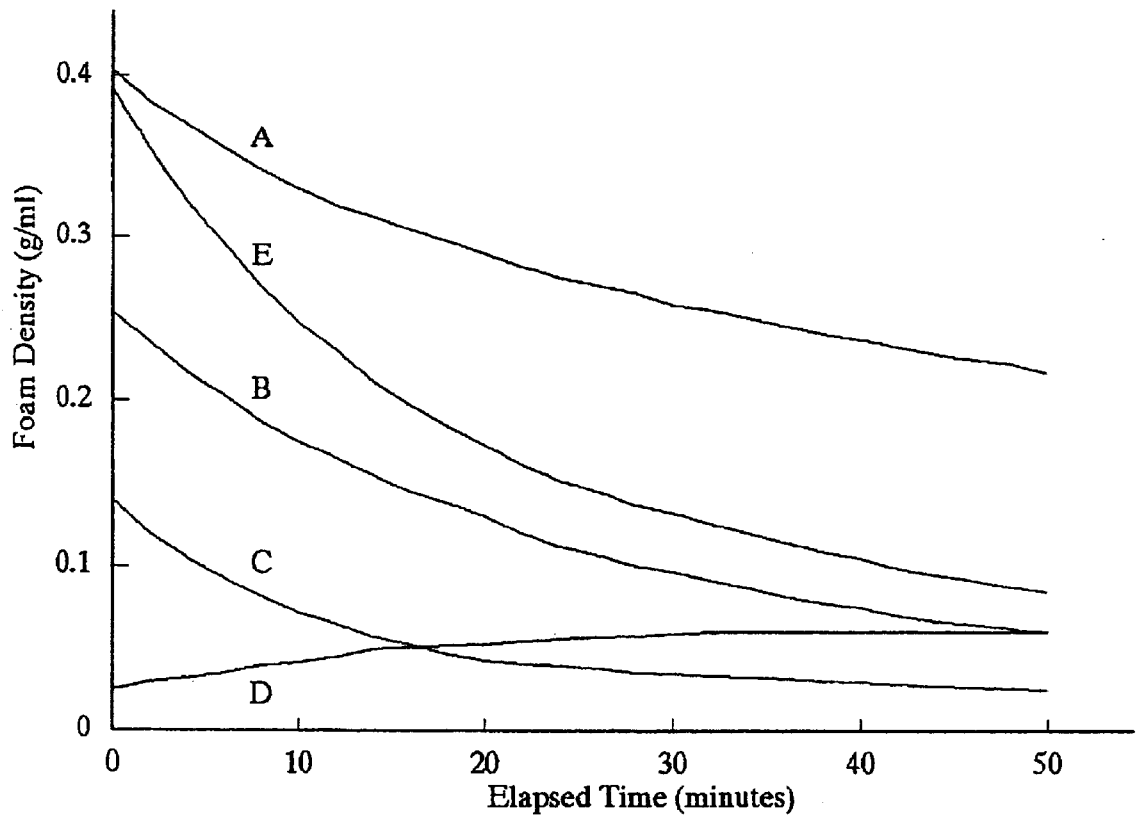

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, as a new paragraph after line 6 add:

*Example 1 of U.S. Pat. No. 4,664,906 lists xanthan gum (an AP) plus hydroxyethyl cellulose (an NCE) plus poloxamer as ingredients in a toothpaste. While these three ingredients are proper components of the surfactant system of the present invention, said Example also contains the ingredient hexedine, a profound foam suppressor. Since all foam suppressors are prohibited by the present invention (see claim 1), U.S. Pat. No. 4,664,906 does not teach the surfactant system of the present invention. In fact, the only surfactant which U.S. Pat. No. 4,664,906 mentions in its claims is the foam suppressor, hexedine.*

AS A RESULT OF REEXAMINATION, IT HAS BEEN DETERMINED THAT:

Claim 7 is cancelled.

Claim 1 is determined to be patentable as amended.

Claims 2–6 and 8–11, dependent on an amended claim, are determined to be patentable.

1. Dental products comprising a *nonirritating* surfactant system [employing] *consisting essentially of* poloxamers as the main surfactant, wherein said poloxamer*s* comprise[s] 0.01 to 10 weight % of said dental product, said system further comprising anionic polysaccharides (AP) plus nonionic cellulose ethers (NCE) in a ternary surfactant system having *greatly* enhanced foaming power relative to poloxamers alone or to poloxamers plus anionic polysaccharide*s* or to poloxamers plus nonionic cellulose ethers, wherein the weight ratio of said poloxamer*s* to said anionic polysaccharides is greater than 1, and the weight ratio of said anionic polysaccharides to said nonionic cellulose ether*s* is greater than 1, *said dental products being essentially free of all surfactants other than those in the ternary surfactant system of poloxamers plus anionic polysaccharides plus nonionic cellulose ethers, and said dental products being essentially free of foam suppressors.*

* * * * *